US007632675B2

(12) United States Patent
Zarur et al.

(10) Patent No.: US 7,632,675 B2
(45) Date of Patent: Dec. 15, 2009

(54) APPARATUS AND METHOD FOR MANIPULATING SUBSTRATES

(75) Inventors: Andrey J. Zarur, Winchester, MA (US); Seth T. Rodgers, Somerville, MA (US); Todd A. Basque, Danvers, MA (US); Ian K. MacGregor, Merrimack, NH (US); Timothy J. Johnson, Andover, MA (US)

(73) Assignee: BioProcessors Corp., Woburn, MA (US)

( * ) Notice: Subject to any disclaimer, the term of this patent is extended or adjusted under 35 U.S.C. 154(b) by 737 days.

(21) Appl. No.: 10/863,584

(22) Filed: Jun. 7, 2004

(65) Prior Publication Data

US 2005/0019904 A1    Jan. 27, 2005

Related U.S. Application Data

(63) Continuation-in-part of application No. 10/456,929, filed on Jun. 5, 2003, now abandoned.

(51) Int. Cl.
*C12M 1/02*    (2006.01)
*C12M 3/02*    (2006.01)

(52) U.S. Cl. .............. 435/287.3; 435/286.2; 435/303.1; 435/303.3; 435/809; 422/64

(58) Field of Classification Search .............. 435/303.1, 435/303.3, 809, 286.2, 287.3; 422/64
See application file for complete search history.

(56) References Cited

U.S. PATENT DOCUMENTS 5,270,205 A    12/1993    Rogalsky (Continued)

FOREIGN PATENT DOCUMENTS

EP    0 164 888 A1    12/1985

(Continued)

OTHER PUBLICATIONS

De Luis, J., Vunjak-Novakovic, G., and Searby N.D. Design and Testing of the ISS Cell Culture Unit. Proc. 51st Congress of the Astronautical Federation, Rio de Janeiro, Oct. 2-6, 2000.

(Continued)

*Primary Examiner*—William H Beisner
(74) *Attorney, Agent, or Firm*—Wolf, Greenfield & Sacks, P.C.

(57) ABSTRACT

This disclosure generally relates to systems and methods for manipulating chambers and other substrates for chemical, biological, or biochemical samples, such as cell culture and other chambers, within units such as incubators. In certain embodiments, the invention provides a technique for maintaining a plurality of substrates or chambers in a housing within which a predetermined environment is maintained, and moving substrates or chambers in and out of the housing, in some cases without creating a large opening in the housing (e.g., by opening a door significantly larger than the substrates). A technique is provided, in certain embodiments, in which a plurality of substrates are mounted in fixed, secured relation to each other within a housing providing a predetermined, controlled environment, and are moved within the housing so that they can be evenly exposed to any differences in environment within the housing. In still another embodiment, the invention provides a method for rotating a substrate or chamber about a substantially vertical and/or horizontal axis.

4 Claims, 11 Drawing Sheets

U.S. PATENT DOCUMENTS

| | | |
|---|---|---|
| 5,340,747 A | 8/1994 | Eden |
| 5,374,395 A | 12/1994 | Robinson et al. |
| 5,424,209 A | 6/1995 | Kearney |
| 5,432,087 A | 7/1995 | Spielmann |
| 5,470,744 A | 11/1995 | Astle |
| 5,576,211 A | 11/1996 | Falkenberg |
| 5,578,269 A | 11/1996 | Yaremko et al. |
| 5,612,188 A | 3/1997 | Shuler et al. |
| 5,945,334 A | 8/1999 | Besemer et al. |
| 5,985,214 A | 11/1999 | Stylli et al. |
| 6,024,921 A * | 2/2000 | Freiner et al. .................. 422/66 |
| 6,050,719 A | 4/2000 | Winkler et al. |
| 6,050,724 A | 4/2000 | Schmitz et al. |
| 6,121,054 A | 9/2000 | Lebl |
| 6,148,878 A | 11/2000 | Ganz et al. |
| 6,193,647 B1 | 2/2001 | Beebe |
| 6,228,636 B1 | 5/2001 | Yahiro et al. |
| 6,264,892 B1 | 7/2001 | Kaltenbach |
| 6,274,384 B1 | 8/2001 | Starzyl et al. |
| 6,360,792 B1 | 3/2002 | Ganz et al. |
| 6,386,749 B1 | 5/2002 | Watts et al. |
| 6,423,536 B1 | 7/2002 | Jovanovich |
| 6,673,595 B2 | 1/2004 | Barbera-Guillem |
| 6,705,754 B2 | 3/2004 | Winkler et al. |
| 2002/0146817 A1 | 10/2002 | Cannon |
| 2003/0040104 A1 | 2/2003 | Barbera-Guillem |
| 2004/0109793 A1 | 6/2004 | McNeely |
| 2006/0019388 A1 | 1/2006 | Hutmacher et al. |

FOREIGN PATENT DOCUMENTS

| | | |
|---|---|---|
| EP | 0 293 782 A1 | 12/1988 |
| WO | WO 91/01365 A1 | 2/1991 |
| WO | WO 99/09394 A1 | 2/1999 |
| WO | WO 2004/108270 A2 | 12/1999 |
| WO | WO 2004/108269 A2 | 12/2004 |
| WO | WO 2004/112946 A2 | 12/2004 |

OTHER PUBLICATIONS

Freed, L., et al., "Tissue engineering of cartilage in space," *Proc. Natl. Acad. Sci.*, 94:13885, 1997.

Vunjack-Novakovic, G., et al., "Microgravity Studies of Cells and Tissues," *Ann NY Acad. Sci.*, 974:504-517, 2002.

Searby, N.D., et al., "Space Life Support From the Cellular Perspective" *ICES Proceedings*, May 2001.

International Search Report, PCT/US2004/018188 mailed Dec. 14, 2004.

Written Opinion, PCT/US/2004/018188 mailed Dec. 14, 2004.

International Preliminary Report on Patentability in PCT/US2004/018183, mailed Dec. 8, 2005.

* cited by examiner

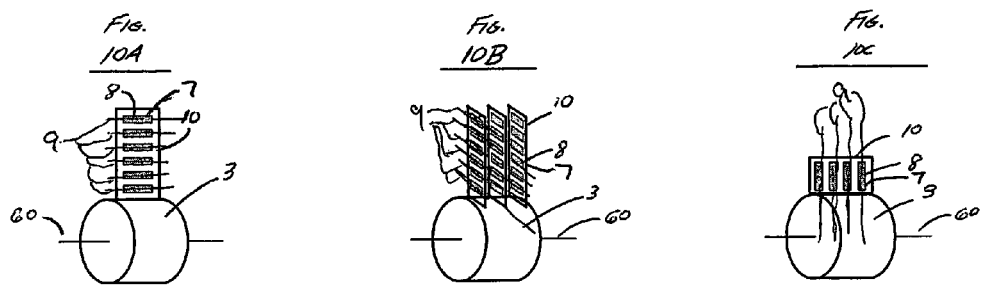

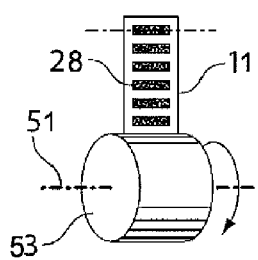
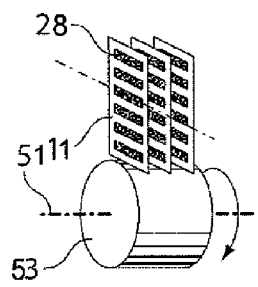
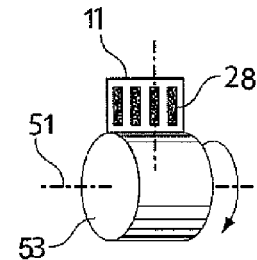
Fig. 11A                Fig. 11B                Fig. 11C
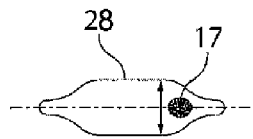
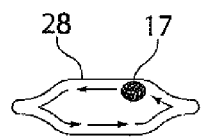
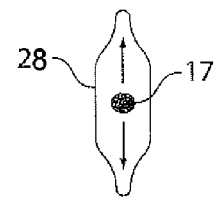
Fig. 12A                Fig. 12B                Fig. 12C

APPARATUS AND METHOD FOR MANIPULATING SUBSTRATES

RELATED APPLICATIONS

This application is a continuation-in-part of U.S. patent application Ser. No. 10/456,929, filed Jun. 5, 2003, now abandoned, entitled "Apparatus and Method for Manipulating Substrates," by Zarur, et al., incorporated herein by reference.

FIELD OF THE INVENTION

Disclosed, generally, are systems and methods for manipulating substrates such as cell culture and other biological, biochemical, or chemical substrates.

BACKGROUND

A variety of apparatuses are known for containing a variety of chemical, biological, and biochemical samples. "Incubators" or, equivalently, "cell culture incubators," as referred to herein, are commonly used for cell and other biological cultures and are configured to be able to maintain the surrounding environment at a certain temperature (e.g., 32° C. or 37° C.), and at a certain relative humidity (e.g., 95% or 100% relative humidity) and/or a certain gas concentration (e.g., an environment comprising 5% or 10% carbon dioxide). Incubators are generally able to maintain these conditions for extended periods of time, for example for days or weeks.

Typically, laboratory incubators have an openable door and a series of shelves inside, as well as sensors for maintaining the internal environment at certain specified values. Upon opening the door, large changes in the internal environment of the incubator may occur, as the outside environment (typically at ambient temperatures and pressure) mixes with the internal environment of the incubator. For example, large shifts in temperature, relative humidity, or gas concentrations can occur within the internal environment of the incubator, which can cause adverse effects on cells or other biological cultures present within the incubator. Reestablishing the proper internal environment within the incubator can take significant time in many cases, which can further adversely affect the cells or other biological cultures.

SUMMARY OF THE INVENTION

This disclosure generally relates to systems and methods for manipulating substrates such as cell culture and other biological, biochemical, or chemical substrates, for example, within incubators. The subject matter of this application involves, in some cases, interrelated products, alternative solutions to a particular problem, and/or a plurality of different uses of a single system or article.

In certain embodiments the invention involves an apparatus. The apparatus, in one set of embodiments, includes a device constructed and arranged to secure and invert a substrate, or an article comprising a substrate, for example, an article comprising at least one biological substrate, chamber or predetermined reaction site. In another set of embodiments, the apparatus includes a device constructed and arranged to rotate and/or revolve a substrate or an article about a substantially horizontal axis. In yet another set of embodiments, the apparatus includes a selection region, and a device able to simultaneously agitate a plurality of substrates or articles, where the device is able to selectively position one of the substrates or articles in the selection region. The term "selection region" as used herein, refers to a region within the apparatus to which or from which a substrate or article, such as a biological substrate, may be transferred to facilitate insertion into or removal from the apparatus. For example, a substrate or article may be transferred to a selection region from a position inside the apparatus (for example, where it is secured to a holder) and then transferred from the selection to a position external of the apparatus. Essentially any suitable technique may be used to transfer the substrate or article to/from the selection region, for example, manual operation by hand, operation by an actuator, robotic actuation, etc.

In still another set of embodiments, the apparatus includes a device constructed and arranged to periodically move a substrate, or an article comprising a substrate, for example, an article comprising at least one biological substrate, chamber or predetermined reaction site, between a first location and a second location vertically aligned with the first location. The substrate or article may comprise, for example, a biological, biochemical, or chemical substrate. The apparatus, in another set of embodiments, includes a cell culture incubator having an interior space, where the cell culture incubator is constructed and arranged to heat the interior space to a temperature of at least about 100° C.

In one embodiment, the apparatus may optionally include a housing including an interior and an exterior, constructed and arranged to enable it to mount a substrate or article, e.g., comprising a chemical, biological, or biochemical sample. The apparatus may also inculde a mechanism configured to be able to maintain the environment within the interior of the housing different from an environment external to the housing; and/or an actuator configured to introduce a substrate or an article from the exterior of the housing into the interior of the housing, and/or to withdraw the substrate or article from the interior of the housing to the exterior of the housing through a port defined in a wall of the housing, where the port includes at least one dimension no more than twice the smallest dimension of the substrate.

In certain embodiments, the invention involves a method. In one set of embodiments, the method includes inverting a substrate or an article comprising a plurality of chemical, biological, and/or biochemical samples, which article is mounted within a housing that can mount a plurality of similar substrates or articles and that can provide environmental control within the housing. The method, in another set of embodiments, includes the step of separating cells from a solution containing the cells, by revolving the solution about a substantially horizontal axis.

In certain embodiments, the invention involves a method of making an apparatus able to manipulate a substrate or article such as a biological, biochemical, or chemical substrate, e.g., as described in-any of the embodiments herein. In certain embodiments, the invention involves a method of using an apparatus able to manipulate a substrate or article such as a biological, biochemical, or chemical substrate, e.g., as described in any of the embodiments herein. In certain embodiments, the invention involves a method of promoting, fabricating, selling, and/or using an apparatus configured to be able to manipulate a substrate or article such as a biological, biochemical, or chemical substrate, e.g., as described in any of the embodiments herein.

Other advantages and novel features of the invention will become apparent from the following detailed description of various non-limiting embodiments of the invention when considered in conjunction with the accompanying drawings, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control. If two (or more) applications incorporated by reference include conflicting and/or inconsistent disclosure with respect to each other, then the later-filed application shall control.

BRIEF DESCRIPTION OF THE DRAWINGS

Non-limiting embodiments of the present invention will be described by way of example with reference to the accompanying drawings in which:

FIGS. 10A-l0C illustrate embodiments demonstrating that certain substrates, for example those comprising a plurality of elongate predetermined reaction sites, can be secured to certain inventive apparatuses in a variety of suitable orientations;

FIGS. 11A-11C illustrate various orientations in which chips may be positioned on a rotating apparatus, and FIGS. 12A-12C show selected movement directions of immiscible substances.

DETAILED DESCRIPTION

Figure 1:
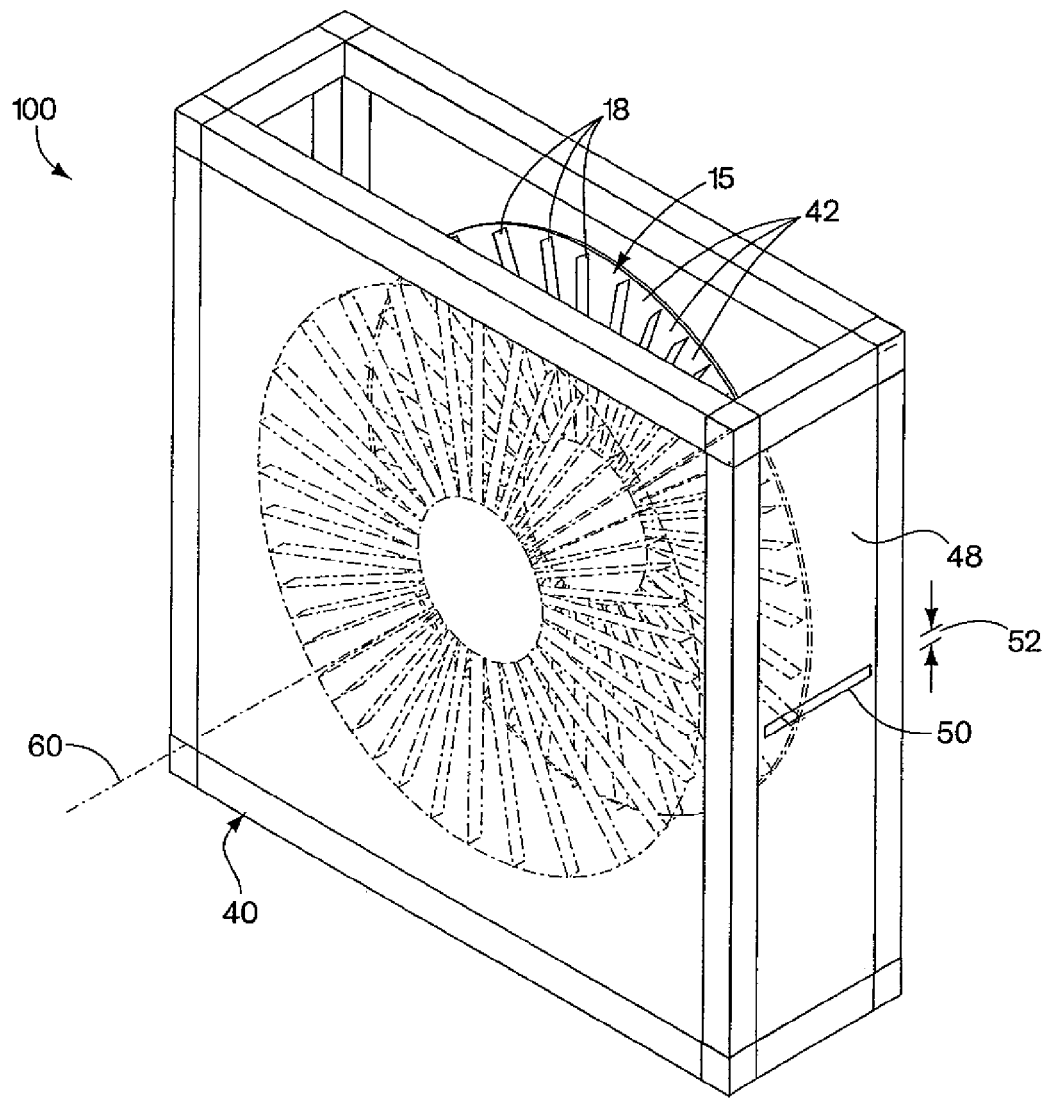
FIG. 1 illustrates an apparatus enclosed within a housing, according to one embodiment of the invention.

This disclosure generally relates to systems and methods for manipulating chambers and other substrates for chemical, biological, or biochemical samples, such as cell culture and other chambers, within units such as incubators. In certain embodiments, the invention provides a technique for maintaining a plurality of substrates or chambers in a housing within which a predetermined environment is maintained, different from the environment external to the housing, and moving substrates or chambers in and out of the housing, in some cases without creating a large opening in the housing (e.g., by opening a door significantly larger than the substrates). A technique is provided, in certain embodiments, in which a plurality of substrates are mounted in fixed, secured relation to each other within a housing providing a predetermined, controlled environment, and are moved within the housing so that they can be evenly exposed to any differences in environment within the housing. In certain embodiments, the invention provides a technique for agitating a fluid within one or more chambers or substrates within a housing that can provide environmental control, in certain embodiments without physically stirring the fluid, such as with a stir bar or other stirring element in direct contact with the fluid. In still another embodiment, the invention provides a method for rotating a substrate or chamber about a substantially vertical and/or horizontal axis. In some cases, any of the above-described systems can be rotated at a speed sufficient to cause separation of a substance within the chamber or substrate.

Each of the following commonly-owned applications directed to related subject matter and/or disclosing methods and/or devices and/or materials useful or potentially useful for the practice of the present invention is incorporated herein by reference: U.S. Provisional Patent Application Ser. No. 60/188,275, filed Mar. 10, 2000, entitled "Microreactor," by Jury, et al.; U.S. patent application Ser. No. 09/707,852, filed Nov. 7, 2000, entitled "Microreactor," by Jury, et al.; International Patent Application No. PCT/US01/07679, filed Mar. 9, 2001, entitled "Microreactor," by Jury, et al., published as WO 01/68257 on Sep. 20, 2001; U.S. Provisional Patent Application Ser. No. 60/282,741, filed Apr. 10, 2001, entitled "Microfermentor Device and Cell Based Screening Method," by Zarur, et al.; U.S. patent application Ser. No. 10/119,917, filed Apr. 10, 2002, entitled "Microfermentor Device and Cell Based Screening Method," by Zarur, et al., published as 2003/0077817 on Apr. 24, 2003; International Patent Application No. PCT/US02/11422, filed Apr. 10, 2002, entitled "Microfermentor Device and Cell Based Screening Method," by Zarur, et al., published as WO 02/083852 on Oct. 24, 2002; U.S. Provisional Patent Application Ser. No. 60/386,323, filed Jun. 5, 2002, entitled "Materials and Reactors having Humidity and Gas Control," by Rodgers, et al.; U.S. Provisional Patent Application Ser. No. 60/386,322, filed Jun. 5, 2002, entitled "Reactor Having Light-Interacting Component," by Miller, et al.; U.S. patent application Ser. No. 10/223,562, filed Aug. 19, 2002, entitled "Fluidic Device and Cell-Based Screening Method," by Schreyer, et al.; U.S. Provisional Patent Application Ser. No. 60/409,273, filed Sep. 9, 2002, entitled "Protein Production and Screening Methods," by Zarur, et al.; U.S. patent application Ser. No. 10/457,048, filed Jun. 5, 2003, entitled "Reactor Systems Responsive to Internal Conditions," by Miller, et al.; U.S. patent application Ser. No. 10/456,934, filed Jun. 5, 2003, entitled "Systems and Methods for Control of Reactor Environments," by Miller, et al.; U.S. patent application Ser. No. 10/456,133, filed Jun. 5, 2003, entitled "Microreactor Systems and Methods," by Rodgers, et al.; U.S. patent application Ser. No. 10/457,049, filed Jun. 5, 2003, entitled "Materials and Reactor Systems having Humidity and Gas Control," by Rodgers, et al,. published as 2004/0058437 on Mar. 25, 2004; International Patent Application No. PCT/US03/17816, filed Jun. 5, 2003, entitled "Materials and Reactor Systems having Humidity and Gas Control," by Rodgers, et al., published as WO 03/103813 on Dec. 18, 2003; U.S. patent application Ser. No. 10/457,015, filed Jun. 5, 2003, entitled "Reactor Systems Having a Light-Interacting Component," by Miller, et al., published as 2004/0058407 on Mar. 25, 2004; International Patent Application No. PCT/US03/18240, filed Jun. 5, 2003, entitled "Reactor Systems Having a Light-Interacting Component," by Miller, et al., published as WO 03/104384 on Dec. 18, 2003; U.S. patent application Ser. No. 10/457,017, filed Jun. 5, 2003, entitled "System and Method for Process Automation," by Rodgers, et al.; U.S. patent application Ser. No. 10/456,929, filed Jun. 5, 2003, entitled "Apparatus and Method for Manipulating Substrates," by Zarur, et al.; U.S. patent application Ser. No. 10/633,448, filed Aug. 1, 2003, entitled "Microreactor," by Jury, et al.; International Patent Application No. PCT/US03/25956, filed Aug. 19, 2003, entitled "Determination and/or Control of Reactor Environmental Conditions," by Miller, et al., published as WO 2004/016727 on Feb. 26, 2004; U.S. patent application Ser. No. 10/664,046, filed Sep. 16, 2003, entitled "Determination and/or Control of Reactor Environmental Conditions," by Miller, et al.; International Patent Application No. PCT/US03/25907, filed Aug. 19, 2003, entitled "Systems and Methods for Control of pH and Other Reactor Environmental Conditions," by Miller, et al., published as WO 2004/016729 on Feb. 26, 2004; U.S. Patent Application Ser. No. 60/498,981, filed Aug. 29, 2003, entitled "Rotatable Reactor Systems and Methods," by Zarur, et al.; U.S. Patent Application Ser. No. 60/499,124, filed Aug. 29, 20003, entitled "Reactor with Memory Component," by Zarur, et al.; U.S. patent application Ser. No. 10/664,068, filed Sep. 16, 2003, entitled "Systems and Methods for Control of pH and Other Reactor Environmental Conditions," by Miller, et al.; International Patent Application No. PCT/US03/25943, filed Aug. 19, 2003, entitled "Microreactor Architecture and Methods," by Rodgers, et al.; a U.S. Patent Application filed on Sep. 16, 2003, entitled "Microreactor Architecture and Methods, " by Rodgers, et al.; a U.S. Patent Application filed on Jun. 7, 2004, entitled "Control of Reactor Environmental Conditions, " by Rodgers, et al.; a U.S. Patent Application filed on Jun. 7, 2004, entitled "System and Method for Process Automation, " by Rodgers, et al.; an International Patent Application filed on Jun. 7, 2004, entitled "System and Method for Process Automation," by Rodgers, et al.; an International Patent Application filed on Jun. 7, 2004, entitled "Apparatus and Method for Manipulating Substrates," by Zarur, et al.; a U.S. Patent Application filed on Jun. 7, 2004, entitled "Reactor with Memory Component, " by Zarur, et al.; an International Patent Application filed on Jun. 7, 2004, entitled "Reactor with Memory Component," by Zarur, et al.; a U.S. Patent Application filed on Jun. 7, 2004, entitled "Gas Control in a Reactor," by Rodgers, et al.; a U.S. Design Patent Application filed on Jun. 7, 2004, entitled "Reactor and Chip," by Russo, et al.; U.S. patent application Ser. No. 11/147,413 filed on Jun. 7, 2004, entitled "Reactor Mixing" by Johnson, et al.; and a U.S. Patent Application filed on Jun. 7, 2004, entitled "Reactor Mixing Apparatus and Method," by MacGregor.

The majority of the description herein is provided in the context of biological species or samples, biological chambers, substrates, and/or articles, and housings that are incubators. It is to be understood that the invention encompasses not only biological samples, but also essentially any chemical or biochemical samples, and chambers and/or substrates for any of these. Those of ordinary skill in the art will recognize the utility of the invention as applied to non-biological samples and chambers or other suitable substrates, and will be able to modify apparatuses described herein, if necessary, for non-biological techniques.

The various aspects of the invention can take the form of many embodiments. In one set of embodiments, a system is provided that includes an apparatus able to invert a chamber, a substrate, and/or an article comprising one or more predetermined reaction sites. As used herein, the term "invert," in the context of a chamber, substrate, or article, refers to turning the chamber, substrate, or article upside down at at least some point during a physical manipulation of the chamber, substrate, or article. In certain embodiments, the system includes an apparatus able to rotate and/or revolve a chamber, substrate, and/or article about a substantially horizontal axis, for example to invert it. Any of the above-mentioned systems may be provided in connection with any of a variety of apparatuses to subject the chamber, substrate, and/or article, and/or a sample within the chamber, substrate, and/or article, to a desired environmental condition, for example, an incubator. In some embodiments, the system includes an autoclavable incubator.

As used herein, "sample" means a portion of a chemical, biological, or biochemical species, living or non-living, organic or inorganic, that is desirably manipulated in some fashion, for example, in the context of environmental control, motion (e.g., agitation), and/or the passage of time. For example, a sample can be something desirably studied in terms how a particular environment or environments, motion, and/or time affects it; a sample can be a reactant, or starting material that is known to change chemically or biologically in response to a particular environment(s), motion, and/or time, which change is promoted via embodiments of the invention; a combination of these, or the like.

As used herein, a "substrate" is an article having a surface in and/or on and/or proximate to which a biological, biochemical, or chemical reaction can take place. A substrate may be planar or substantially planar, although in some cases, the substrate may be curved or otherwise non-planar, depending on the specific application. Non-limiting examples of materials useful for forming substrates can include glass, plastic, semiconductor materials, or the like. In some cases, the substrate may be modified to promote or inhibit certain reactions. For example, the substrate may be etched or coated with a chemical that enhances the hydrophobicity or hydrophilicity of the substrate, enhances the cytophobicity or cytophilicity of the substrate, promotes specific or non-specific binding of a reactant to or proximate the substrate, etc. The substrate may be at least partially enclosed in certain embodiments (e.g., as part of a chamber, or contained within a chamber), for example, as in a flask or an enclosed microfluidic system. In some cases, a reaction on a substrate may be altered in some fashion by the addition of a fluid, for example by causing or preventing a reaction in and/or on and/or proximate to the substrate, and/or promoting or inhibiting such reaction. A "chamber," as used herein, is an article having or containing a substrate, and in some cases, may enclose or at least partially enclose the substrate. For example, the chamber may enclose a substrate therein, a substrate may define a wall of the chamber, etc.

A "biological substrate," as used herein, is an article having a surface in and/or on and/or proximate to which a biological reaction can take place. A "biological chamber" is an article having or containing a substrate (e.g., as part of a chamber, or contained within a chamber) in which a biological system can be grown in vitro, for example, cells, tissue and tissue constructs, ex vivo systems, organisms, and the like. A biological chamber typically is enclosed or at least partially enclosed. The chamber may be formed out of any suitable material able to contain cells or other biological systems and/or may include a substrate that cells or other biological systems can adhere to, for example, a substrate comprising glass, polystyrene, and/or other materials known to those of ordinary skill in the art. A "cell culture chamber" is a biological chamber in which cells can be grown in vitro. The substrate typically is planar. Cell culture chambers are well-known in the art and include, but are not limited to, petri dishes (having any suitable diameter), flasks (e.g., T25 flasks, T75 flasks, T150 flasks, T175 flasks, etc.), microplates such as those defined in the 2002 SPS/ANSI proposed standard (e.g., a microplate having dimensions of roughly 127.76±0.50 mm by 85.48±0.50 mm), for example, 6-well microplates, 24-well microplates, 96-well microplates, etc.), and the like. The cell culture chamber may be formed out of any suitable material able to contain cells and allow cell culture to occur, for example, glass, polystyrene and/or other polymers, and/or materials known to those of ordinary skill in the art. In some cases, the cell culture chamber may be disposable.

One example of a biological chamber is a microplate. A "microplate" is also sometimes referred to as a "microtiter" plate, a "microwell" plate, or other similar terms known to the art. The microplate can have standardized or art-recognized dimensions, for example, as defined in the 2002 SPS/ANSI proposed standard (e.g., a microplate having dimensions of roughly 127.76±0.50 mm by 85.48±0.50 mm). The microplate may include any number of wells. For example, as is typically used commercially, the microplate may be a six-well microplate, a 24-well microplate, a 96-well microplate, a 384-well microplate, or a 1,536-well microplate. The wells may each be of any suitable shape, for example, cylindrical or rectangular. The microplate may also have other numbers of wells and/or other well geometries or configurations, for instance, in certain specialized applications.

As used herein, a "reactor" is the combination of components including a reaction site, any chambers (including reaction chambers and ancillary chambers), channels, ports, inlets and/or outlets (i.e., leading to or from a reaction site), sensors, actuators, processors, controllers, membranes, and the like, which, together, operate to contain, promote and/or monitor a biological, chemical, and/or biochemical reaction, interaction, operation, or experiment at a reaction site, and which can be part of a chip. For example, a chip may include at least 5, at least 10, at least 20, at least 50, at least 100, at least 500, or at least 1,000 or more reactors. Examples of reactors include chemical or biological reactors and cell culturing devices, as well as the reactors described in International Patent Application No. PCT/US01/07679, filed Mar. 9, 2001, entitled "Microreactor," by Jury, et al., published as WO 01/68257 on Sep. 20, 2001, incorporated herein by reference. Reactors can include one or more reaction sites or compartments. The reactor may be used for any chemical, biochemical, and/or biological purpose, for example, cell growth, pharmaceutical production, chemical synthesis, hazardous chemical production, drug screening, materials screening, drug development, chemical remediation of warfare reagents, or the like. For example, the reactor may be used to facilitate very small scale culture of cells or tissues. In one set of embodiments, a reactor of the invention comprises a matrix or substrate of a few millimeters to centimeters in size, containing channels with dimensions on the order of, e.g., tens or hundreds of micrometers. Reagents of interest may be allowed to flow through these channels, for example to a reaction site, or between different reaction sites, and the reagents may be mixed or reacted in some fashion. The products of such reactions can be recovered, separated, and treated within the reactor or chip in certain cases.

A "chemical, biological, or biochemical reactor chip," (also referred to, equivalently, simply as a "chip") as used herein, is an integral article that includes one or more reactors. "Integral article" means a single piece of material, or assembly of components integrally connected with each other. As used herein, the term "integrally connected," when referring to two or more objects, means objects that do not become separated from each other during the course of normal use, e.g., cannot be separated manually; separation requires at least the use of tools, and/or by causing damage to at least one of the components, for example, by breaking, peeling, etc. (separating components fastened together via adhesives, tools, etc.).

Many embodiments and arrangements of the disclosed devices are described with reference to a chip, or to a reactor, and those of ordinary skill in the art will recognize that the presently disclosed subject matter can apply to either or both. For example, a channel arrangement may be described in the context of one, but it will be recognized that the arrangement can apply in the context of the other (or, typically, both: a reactor which is part of a chip). It is to be understood that all descriptions herein that are given in the context of a reactor or chip apply to the other, unless inconsistent with the description of the arrangement in the context of the definitions of "chip" and "reactor" herein. It should also be understood that the chips and reactors disclosed herein may have a wide variety of different configurations. For example, a chip may be formed from a single material, or the chip may contain more than one type of reactor, reservoir and/or agent.

As used herein, a "reaction site" is defined as a site within a reactor, chip, chamber, or other article that is constructed and arranged to produce a physical, chemical, biochemical, and/or biological reaction during use of the reactor, chip, chamber, or article. More than one reaction site may be present within a reactor, chip, chamber, or article in some cases, for example, at least one reaction site, at least two reaction sites, at least three reaction sites, at least four reaction sites, at least 5 reaction sites, at least 7 reaction sites, at least 10 reaction sites, at least 15 reaction sites, at least 20 reaction sites, at least 30 reaction sites, at least 40 reaction sites, at least 50 reaction sites, at least 100 reaction sites, at least 500 reaction sites, or at least 1,000 reaction sites or more may be present within a reactor, chip, chamber, or article. The reaction site may be defined as a region where a reaction is allowed to occur; for example, a reactor may be constructed and arranged to cause a reaction within a channel, one or more compartments, at the intersection of two or more channels, etc. The reaction may be, for example, a mixing or a separation process, a reaction between two or more chemicals, a light-activated or a light-inhibited reaction, a biological process, and the like. In some embodiments, the reaction may involve an interaction with light that does not lead to a chemical change, for example, a photon of light may be absorbed by a substance associated with the reaction site and converted into heat energy or re-emitted as fluorescence. In certain embodiments, the reaction site may also include one or more cells and/or tissues. Thus, in some cases, the reaction site may be defined as a region surrounding a location where cells are to be placed within the reactor, chip, chamber, or article, for example, a cytophilic region within the reactor, chip, chamber, or article.

As used herein, a "channel" is a conduit associated with a reactor and/or a chip (within, leading to, or leading from a reaction site) that is able to transport one or more fluids specifically from one location to another, for example, from an inlet of the reactor or chip to a reaction site, e.g., as further described below. Materials (e.g., fluids, cells, particles, etc.) may flow through the channels, continuously, randomly, intermittently, etc. The channel may be a closed channel, or a channel that is open, for example, open to the external environment surrounding the reactor or chip containing the reactor. The channel can include characteristics that facilitate control over fluid transport, e.g., structural characteristics (e.g., an elongated indentation), physical/chemical characteristics (e.g., hydrophobicity vs. hydrophilicity) and/or other characteristics that can exert a force (e.g., a containing force) on a fluid when within the channel. The fluid within the channel may partially or completely fill the channel. In some cases the fluid may be held or confined within the channel or a portion of the channel in some fashion, for example, using surface tension (i.e., such that the fluid is held within the channel within a meniscus, such as a concave or convex meniscus). The channel may have any suitable cross-sectional shape that allows for fluid transport, for example, a square channel, a circular channel, a rounded channel, a rectangular channel (e.g., having any aspect ratio), a triangular channel, an irregular channel, etc. The channel may be of any size within the reactor or chip. For example, the channel may have a largest dimension perpendicular to a direction of fluid flow within the channel of less than about 1000 micrometers in some cases, less than about 500 micrometers in other cases, less than about 400 micrometers in other cases, less than about 300 micrometers in other cases, less than about 200 micrometers in still other cases, less than about 100 micrometers in still other cases, or less than about 50 or 25 micrometers in still other cases. In some embodiments, the dimensions of the channel may be chosen such that fluid is able to freely flow through the channel, for example, if the fluid contains cells. The dimensions of the channel may also be chosen in certain cases, for example, to allow a certain volumetric or linear flowrate of fluid within the channel. In one embodiment, the depth of other largest dimension perpendicular to a direction of fluid flow may be similar to that of a reaction site to which the channel is in fluid communication with. Of course, the number of channels, the shape or geometry of the channels, and the placement of channels within the chip can be determined by those of ordinary skill in the art.

In some embodiments of the invention, a sample can be agitated without being physically stirred, such as by a stir bar or other stirring element in physical contact with the sample. "Agitated," as used herein, refers to any active process able to cause the mixing of fluids of a sample, for example, within a predetermined reaction site, through processes such as physical stirring of the fluids, vibration of the predetermined reaction site, rotation of the predetermined reaction site, or of the chip or substrate containing the predetermined reaction site (which then induces rotational flow of the fluids within the predetermined reaction site, thus causing mixing to occur), or the like. The agitation may be direct (e.g., directly applied to the fluid) or indirect (e.g., applied to the chip or substrate containing the fluid). The agitation of the fluid may be manually or mechanically controlled in some fashion, as is known to those of ordinary skill in the art. As used herein, "physically stirring" refers to the agitation of fluids within the predetermined reaction site with active mixing elements. "Active mixing elements," as used herein, is meant to define mixing elements such as blades, stirrers, impellers, or the like which are movable relative to the predetermined reaction site itself, i.e., movable relative to walls defining a reaction site within a chip or substrate.

Where a substrate such as a chip is used, some portion or all of it may be treated in such a way as to promote attachment of cells or promote or facilitate biological cultures (e.g., a "biological substrate"). For example, a substrate may be ionized and/or coated with any of a wide variety of hydrophilic, cytophilic, and/or biophilic materials, for example, materials having exposed carboxylic acid, alcohol, and/or amino groups. In other embodiments, the surface of the substrate may be at least partially coated with a biological material that promotes adhesion, for example, fibronectin, laminin, vitronectin, albumin, collagen, and/or a peptide containing an RGD sequence. Other suitable hydrophilic, cytophilic, and/or biophilic materials will be known to those of ordinary skill in the art.

In embodiments in which a cell culture chamber is used, it may include a substrate suitable for growing a cell type that can be cultured in vitro, for example, a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some embodiments, more than one cell type may be used simultaneously, for example, fibroblasts and hepatocytes. In certain embodiments, cell monolayers, tissue cultures or cellular constructs (e.g., cells located on a non-living scaffold), and the like may also be used in the reaction site. In some cases, the cell may be a genetically engineered cell. In certain embodiments, the cell may be a Chinese hamster ovarian ("CHO") cell or a 3T3 cell. In some embodiments, more than one cell type may be used simultaneously, for example, fibroblasts and hepatocytes. In certain embodiments, cell monolayers, tissue cultures or cellular constructs (e.g., cells located on a non-living scaffold), and the like may also be used in the reaction site. The precise environmental conditions necessary in the reaction site for a specific cell type or types may be readily determined by those of ordinary skill in the art.

In some instances, the cells may produce chemical or biological compounds of therapeutic and/or diagnostic interest. For example, the cells may be able to produce products such as monoclonal antibodies, proteins such as recombinant proteins, amino acids, hormones, vitamins, drug or pharmaceuticals, other therapeutic molecules, artificial chemicals, polymers, tracers such as GFP ("green fluorescent protein") or luciferase, etc. In one set of embodiments, the cells may be used for drug discovery and/or drug developmental purposes. For instance, the cells may be exposed to an agent suspected of interacting with the cells. Non-limiting examples of such agents include a carcinogenic or mutagenic compound, a synthetic compound, a hormone or hormone analog, a vitamin, a tracer, a drug or a pharmaceutical, a virus, a prion, a bacteria, etc. For example, in one embodiment, the invention may be used in automating cell culture to enable high-throughput processing of monoclonal antibodies and/or other compounds of interest. In another embodiment, the invention may be used for drug screening purposes.

In certain embodiments of the invention, the cell culture or other biological chamber (or other substrate), such as a chip, or volumetric container(s) defining reaction site(s) thereof, may be substantially "watertight," i.e., the chamber, etc. may be constructed and arranged such that a liquid inside the chamber, etc. such as water, does not come out of the chamber, etc. regardless of the its orientation or position. For example, if the chamber is a flask, the flask may have a screw-on cap that can be attached to the flask to prevent liquids from coming out. As another example, the chamber may comprise at least a portion of an article such as a sealed microplate, optionally with internal access to the microplate through self-sealing ports able to allow internal access, for example, when punctured with a needle. Non-limiting examples of self-sealing materials suitable for use with the invention include, for example, polymers such as polydimethylsiloxane ("PDMS"), or silicone materials such as Formulations RTV 108, RTV 615, or RTV 118 (General Electric, New York, N.Y.).

In one set of embodiments, the chamber or other substrate may be a microfluidic chamber or substrate (e.g., a chamber or substrate having at least one fluidic pathway therein having a smallest cross-sectional dimension of less than about 1 mm). The microfluidic chamber may be sealed in some cases and/or define spaces that are enclosed such that the chamber can be inverted without releasing any liquids contained therein. Non-limiting examples of microfluidic chambers and other substrates include those disclosed in International Patent Application No. PCT/US01/07679, filed Mar. 9, 2001, entitled "Microreactor," by Jury, et al., published as WO 01/68257 on Sep. 20, 2001; U.S. patent application Ser. No. 09/707,852, filed Nov. 7, 2000, entitled "Microreactor," by Jury, et al.; U.S. patent application Ser. No. 10/119,917, filed Apr. 10, 2002, entitled "Microfermentor Device and Cell Based Screening Method," by Zarur, et al., published as 2003/0077817 on Apr. 24, 2003; U.S. Provisional Patent Application Ser. No. 60/386,323, filed Jun. 5, 2002, entitled "Materials and Reactors having Humidity and Gas Control," by Rodgers, et al.; U.S. Provisional Patent Application Ser. No. 60/386,322, filed Jun. 5, 2002, entitled "Reactor Having Light-Interacting Component," by Miller, et al.; U.S. patent application Ser. No. 10/457,048, filed Jun. 5, 2003, entitled "Reactor Systems Responsive to Internal Conditions," by Miller, et al.; U.S. patent application Ser. No. 10/456,934, filed Jun. 5, 2003, entitled "Systems and Methods for Control of Reactor Environments," by Miller, et al.; U.S. patent application Ser. No. 10/456,133, filed Jun. 5, 2003, entitled "Microreactor Systems and Methods," by Rodgers, et al.; U.S. patent application Ser. No. 10/457,049, filed Jun. 5, 2003, entitled "Materials and Reactor Systems having Humidity and Gas Control," by Rodgers, et al,. published as 2004/0058437 on Mar. 25, 2004; U.S. patent application Ser. No. 10/457,015, filed Jun. 5, 2003, entitled "Reactor Systems Having a Light-Interacting Component," by Miller, et al., published as 2004/0058407 on Mar. 25, 2004, a U.S. Patent Application filed on even date herewith, entitled "Gas Bubble Control in Microreactors"; and a U.S. Patent Application filed on even date herewith, entitled "Reactor Mixing Via Bubble Control," all of which are incorporated herein by reference.

Figure 2:
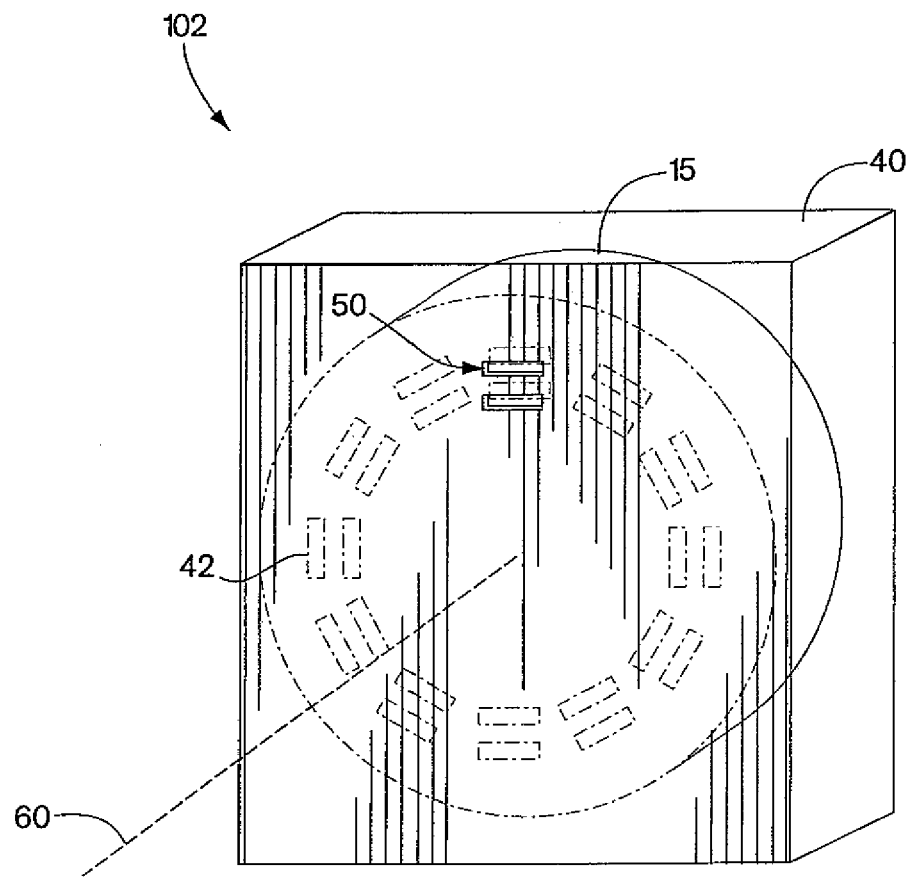
FIG. 2 illustrates an apparatus enclosed within a housing, according to another embodiment of the invention.

As used herein, "secure" means to affix an object to an apparatus such that the object will not be dislodged from the apparatus due to motion of the apparatus. For example, the apparatus may invert, rotate, revolve, agitate, stir, and/or vibrate the object without dislodging it. The object, in certain embodiments, may be intentionally removed from the apparatus by an operator (e.g., a mechanical or automated device, or a human user). As one example, a chamber or other substrate may be placed into a slot of an apparatus designed to secure the chamber or other substrate during use of the apparatus. For instance, as is shown in FIGS. 1 and 2, a chamber (or other substrate) may be inserted into an apparatus in a slot 42 designed to hold the chamber, thereby securing the chamber within the apparatus. Optionally, mechanical restraints, such as hooks, guides, clips, fasteners, bands, or springs may be used to secure the chamber to the apparatus. As another example, a chamber may be secured to an apparatus via a clamp. In some cases, a chamber may be secured in an apparatus in such a way that the chamber is able to move within the apparatus in some fashion, without being dislodged from the apparatus due to motion of the apparatus.

Many embodiments and arrangements of the disclosed devices are described with reference to a chamber, or to a substrate, and those of ordinary skill in the art will recognize that the presently disclosed subject matter can apply to either or both. Thus, it should be understood that all descriptions herein that are given in the context of a chamber or substrate apply to the other, unless inconsistent with the description of the arrangement in the context of the definitions of "chamber" and "substrate" herein.

In one aspect, the invention includes an apparatus configured to be able to invert a chamber (or other substrate). The chamber may be positioned within the apparatus in any suitable orientation, for example, as shown in FIG. 10. The chamber may be inverted, for example, to insure adequate mixing of the contents of the chamber. In some cases, the apparatus may be configured to be able to repeatedly invert the chamber, for example, at a fixed frequency, or when desired, such as in response to a certain stimulus or condition, or when desired by an operator. If the chamber is a cell culture chamber, the chamber may be inverted, for example, to supply mechanical forces to the cells (e.g., if the cells are susceptible to, or stimulated by, certain mechanical forces, such as certain types of cardiac or other hematopoetic cells), to maintain a suitable air-liquid interface for cells stimulated by such interfaces (for example, skin cells), and the like. In one set of embodiments where the apparatus is positioned within an incubator (or other surrounding housing), the apparatus may invert the chamber to ensure adequate mixing or exposure of the chamber to the environment within the surrounding incubator.

Figure 5:
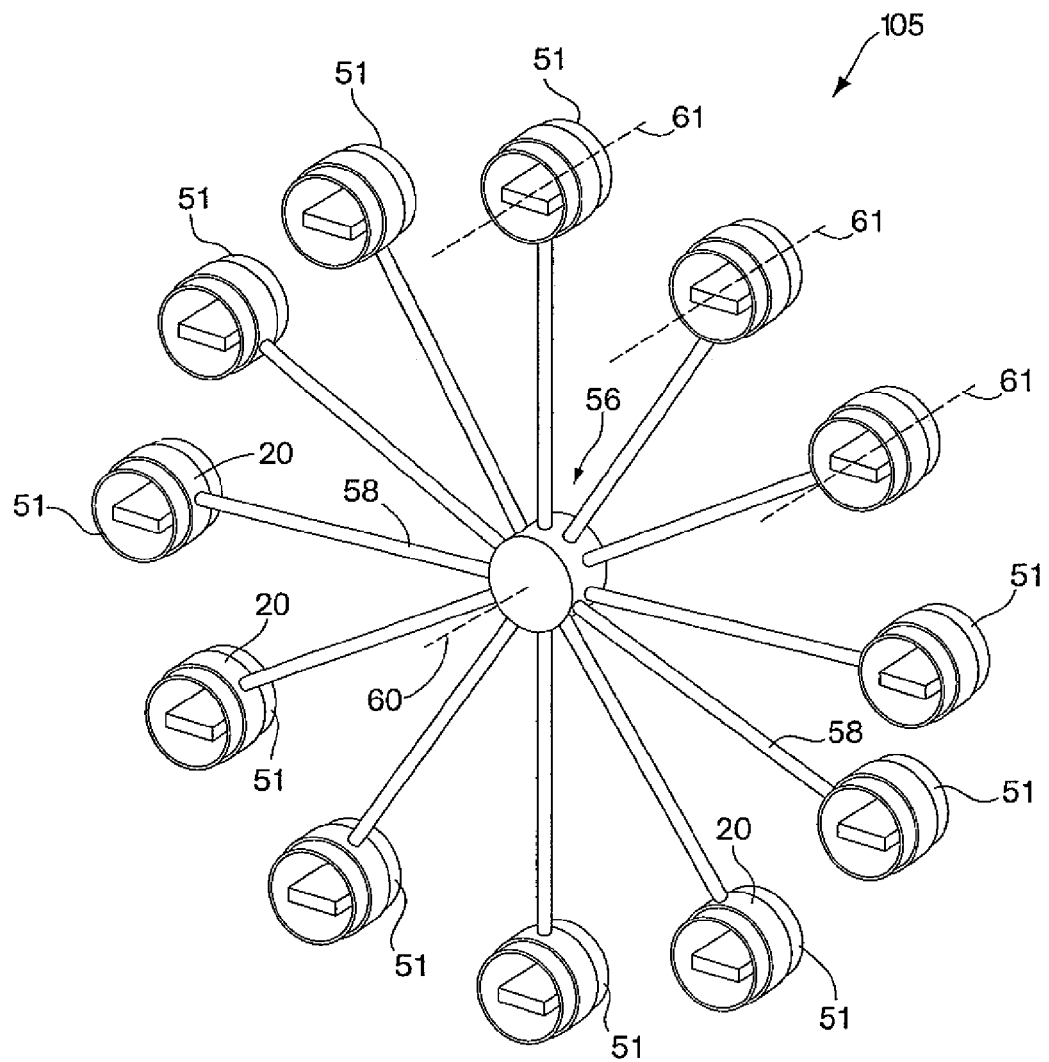
FIG. 5 illustrates an embodiment of the invention configured to be able to simultaneously rotate and revolve substrates.

In another aspect of the invention, the apparatus is configured to be able to cause the chamber (or other substrate) to be rotated and/or revolved about a substantially horizontal axis. As used herein, an object that is "rotated" is turned about an axis located internally of the object, while an object that is "revolved" is turned about an axis located externally of the object. In certain embodiments, for example, as shown in FIG. 5, an apparatus of the invention may be configured to be able to simultaneously rotate a chamber about a first substantially horizontal axis 61 and revolve the chamber about a second substantially horizontal axis 60. (In the embodiment shown in FIG. 5, the second substantially horizontal axis itself is revolved around the first substantially horizontal axis.) As used herein, a "substantially horizontal axis" is generally an axis that is parallel or nearly parallel to the ground. For example, the substantially horizontal axis may be at an angle that is less than 20° with respect to the ground, less than 10° with respect to the ground, less than 5° with respect to the ground, or less than 1° with respect to the ground. In one set of embodiments, the rotation and/or revolution of the chamber (or other substrate) within the apparatus may be designed such that the chamber (or other substrate) remains substantially level with respect to the ground during use of the apparatus, for example, as in the embodiment illustrated in FIG. 5.

Figure 9:
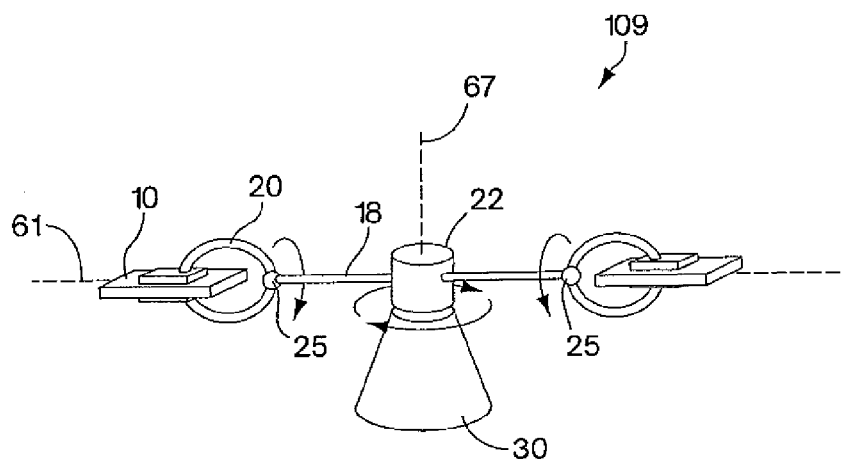
FIG. 9 illustrates another embodiment of the invention configured to be able to revolve a substrate about more tan one axis simultaneously.

In certain embodiments of the invention, the apparatus is configured to be able to agitate at least a portion of the contents within the chamber (or other substrate), for example, by causing stirring or mixing in the contents due to motion of the chamber or substrate. For instance, the apparatus may vibrate a substrate, or cause rotation and/or revolution of a substrate about one or more axes, for example as illustrated in FIG. 9.

FIG. 1 shows an example of an apparatus 100 for manipulating a chemical, biological, or biochemical sample in accordance with a variety of embodiments of the present invention. Apparatus 100, and other arrangements shown in the figures, are intended to be exemplary only. Other arrangements are possible and are embraced by the present invention. Apparatus 100 includes a housing 40 of generally rectangular solid shape (although the apparatus itself is not solid). In the embodiment illustrated, apparatus 100 includes two, generally square, opposed major surfaces joined by four edges of rectangular shape. Housing 40 may be, for example, an incubator. In some cases, housing 40 may be sufficiently enclosed so as to keep device 15 clean, free of dust particles, within a laminar flow field, sterile, etc., depending on the application.

Mounted within housing 40, on an axis 60 passing through the two, opposed major surfaces of the housing is a device 15 for securing a plurality of individual chambers or other substrates which may be constructed and arranged to contain a sample or a plurality of samples. Device 15 takes the form of a rotatable wheel with a plurality of radially outwardly extending members 18 which define, therebetween, a plurality of slots 42 within which one or more chambers can be positioned. Once the chambers are secured within slots 42, device 15 can be rotated, manually or automatically, about axis 60, thereby periodically inverting the chambers secured in slots 42. In some cases, device 15 can be rotated at a speed sufficient to cause (or prevent) separation of a substance within the chamber or substrate (i.e., "centrifugation"). For example, if a chamber within device 15 contains a solution containing cells, then device 15 may be rotated at a speed sufficient to cause sedimentation of the cells from the solution, for instance, at a speed of about 400 rpm, about 600 rpm, about 800 rpm, about 1000 rpm, about 1200 rpm, etc. As another example, if a chamber within device 15 contains cells, then device 15 may be rotated at a speed sufficient to cause separation of the internal components of the cells (i.e., into organelles).

It will be observed that if the environment (e.g., humidity, temperature, exposure to light, etc.) within housing 40 is non-uniform, chambers secured by slots 42 and rotated about axis 60 will be exposed more uniformly to any differences in the environment within housing 40. Additionally, it can be seen that the contents of the chambers can be agitated without the need for any physical stirring.

Within one face 48 of housing 40, which defines one of the edges of the housing joining the opposed major surfaces, is an access port 50 through which a chamber (or other substrate) can be introduced into and/or removed from the interior of housing 40. Access port 50 may be positioned anywhere within housing 40 that allows suitable access of chambers or other substrates to apparatus 100, for example, in a side of housing 40, or on one or more major surfaces of housing 40 (e.g., as shown in FIG. 2). For the insertion of a chamber into device 15 to be secured within a slot 42 of device 15, device 15 can be rotated so that a desired slot is aligned with access port 50, and a chamber is inserted through access port 50 to be secured by a slot 42 within a selection region. Device 15 can be rotated to any predetermined radial orientation aligning a desired slot 42, with access to access port 50, so that one or more chambers can be positioned within predetermined slots 42, and their location known so the chambers can be removed from device 15 such that a predetermined slot securing a predetermined chamber is aligned with access port 50 for external removal (for example, within a selection region). The chambers (or other substrates) can be inserted into and/or removed from housing 40 via slot 50 by essentially any technique, including manual operation by hand, operation by an actuator, robotic actuation, etc., as described more fully below. Access port 50 can be an opening in wall 48 of the housing, optionally including a flap, door, or other member that allows access port 50 to be closed when not being used to introduce or remove a chamber from the housing, for instance, to maintain the environment within the housing, to maintain cleanliness and/or sterility within the housing, or the like. Additional arrangements are described below.

Although it need not be, apparatus 100, and similar apparatus described herein, can define a module of a cluster-tool type apparatus designed to manipulate chemical, biological, or biochemical samples, or similar systems as described in U.S. patent application Ser. No. 10/457,017, filed Jun. 5, 2003, entitled "System and Method for Process Automation," by Rodgers, et al., or a U.S. Patent Application filed on even date herewith, entitled "System and Method for Process Automation," by Rodgers, et al., each incorporated herein by reference.

As noted above, certain embodiments of the invention involve introducing and removing samples from a housing without creating a large opening in the housing (e.g., by opening a large door of the housing), and thereby disrupting the environment within the housing. Access port 50 represents one such embodiment. In one set of embodiments, port 50 includes a minimum cross-sectional dimension 52 that is no greater than 4 times the minimum dimension of a chamber or other substrate introduced through access port 50 into housing 40. Alternatively, the minimum dimension can be no more than 3 times, 2 times, or 1.5 times the minimum dimension of a chamber or substrate introduced into housing 40 through port 50. As used herein, the "minimum dimension" is the distance between two parallel, imaginary planes, positioned as close to each other as possible, between which the entire substrate can reside. Defined another way in connection with a generally rectangular solid shape, having a length, width, and height or thickness, the height or thickness of the shape defines the minimum dimension and is less than each of the length and width.

Referring now to FIG. 2, another embodiment of an alternate apparatus 102 is illustrated. Apparatus 102 is similar to apparatus 100 in FIG. 1, except that device 15 is constructed such that slots are addressable in a direction parallel to axis 60 about which device 15 rotates. That is, slots 42 are positioned in a side of device 15 that is parallel to a major face of housing 40. In this arrangement, access ports 50 are positioned in one of the opposed major faces of housing 40, and can be aligned with slots 42. In the embodiment illustrated, two sets of slots 42 are positioned at two different distances radially outwardly from axis 60, and two access ports 50 are positioned in a major face of housing 40 so as to be alignable with each of the two sets of slots 42.

Figure 3:
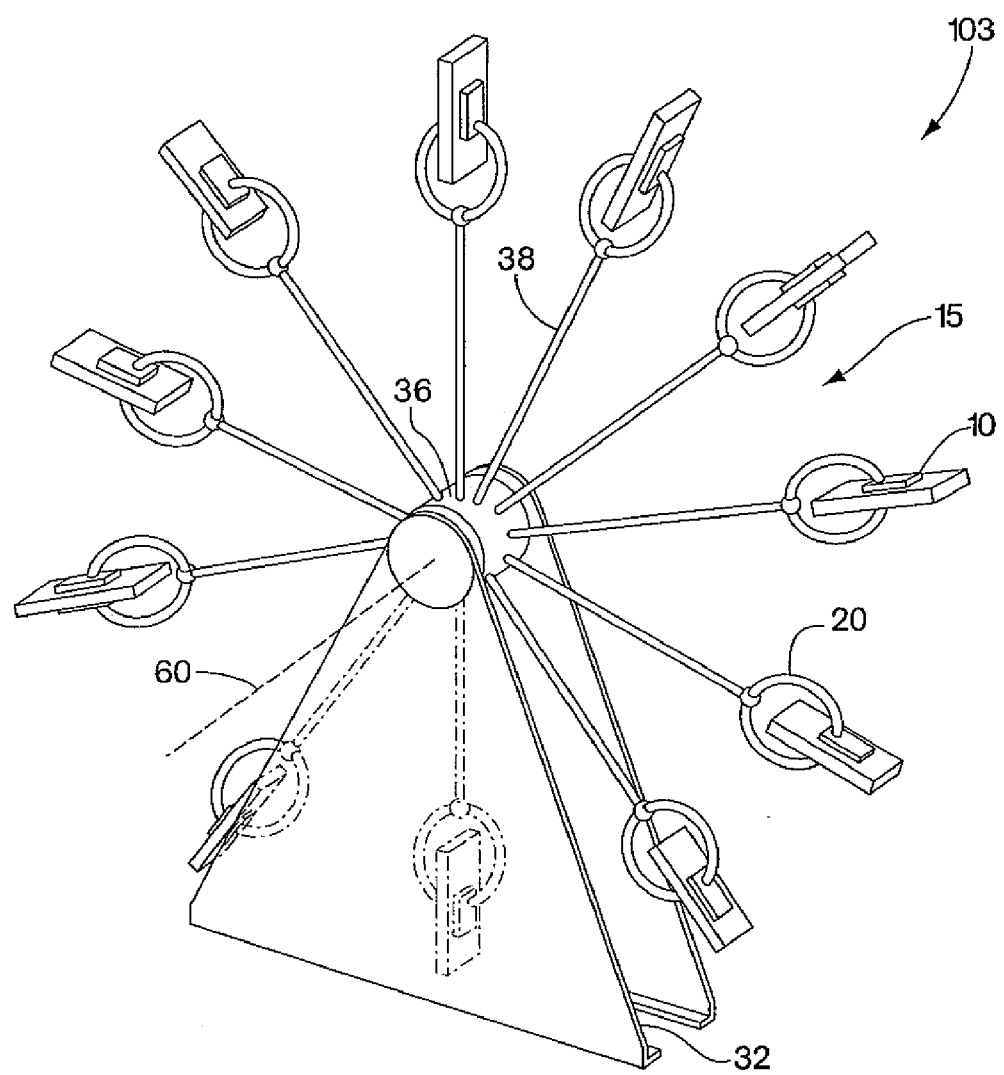
FIG. 3 illustrates a free-standing embodiment of the invention.

FIG. 3 shows an embodiment of the invention including an apparatus 103 that is free-standing, i.e., not connected to a housing, incubator, or other supporting structure. For example, the embodiment shown in FIG. 3 could be positioned on the floor, or on the surface of a bench or counter. In FIG. 3, apparatus 103 includes a rotating device 15 having a plurality of radially outwardly extending members 38, where each member 38 contains a securing mechanism able to secure chambers 10. In this example, the mechanism to secure chambers 10 is a clamp 20. Clamp 20 may be any mechanical or electromechanical clamp able to secure chambers 10. Of course, other methods of securing chambers 10 to members 38 may be used as well, and are known to those of ordinary skill in the art, for example, a detent mechanism, protrusions insertable into corresponding indentations in a substrate or chamber containing the sample, or the like. Each of the radially outwardly extending members 38 in FIG. 3 is connected to an axle 36 able to rotate about substantially horizontal axis 60. Other embodiments of the invention may contain more or fewer radially outwardly extending members than those depicted in FIG. 3; additionally, in some cases, not all of radially outwardly extending members may contain a clamp or other securing mechanisms, or some of the radially outwardly extending members may contain more than one clamp or other securing mechanisms.

In FIG. 3, stand 32 supports an axle 36, and positions axle 36 in such a way as to allow axle 36 to rotate about substantially horizontal axis 60. The mechanism for rotating axle 36 about substantially horizontal axis 60 (as well as similar mechanisms for use with devices, according to other embodiments) may be mechanically or computer controlled in some cases; in other cases, the mechanism may be manually controlled. Stand 32 in FIG. 3 is constructed and arranged in such a way as to allow sufficient clearance for radially outwardly extending members 38, when holding chambers 10, to revolve under substantially horizontal axis 60 without interference, e.g., with a surface upon which stand 32 rests, or with stand 32 itself.

Figure 4:
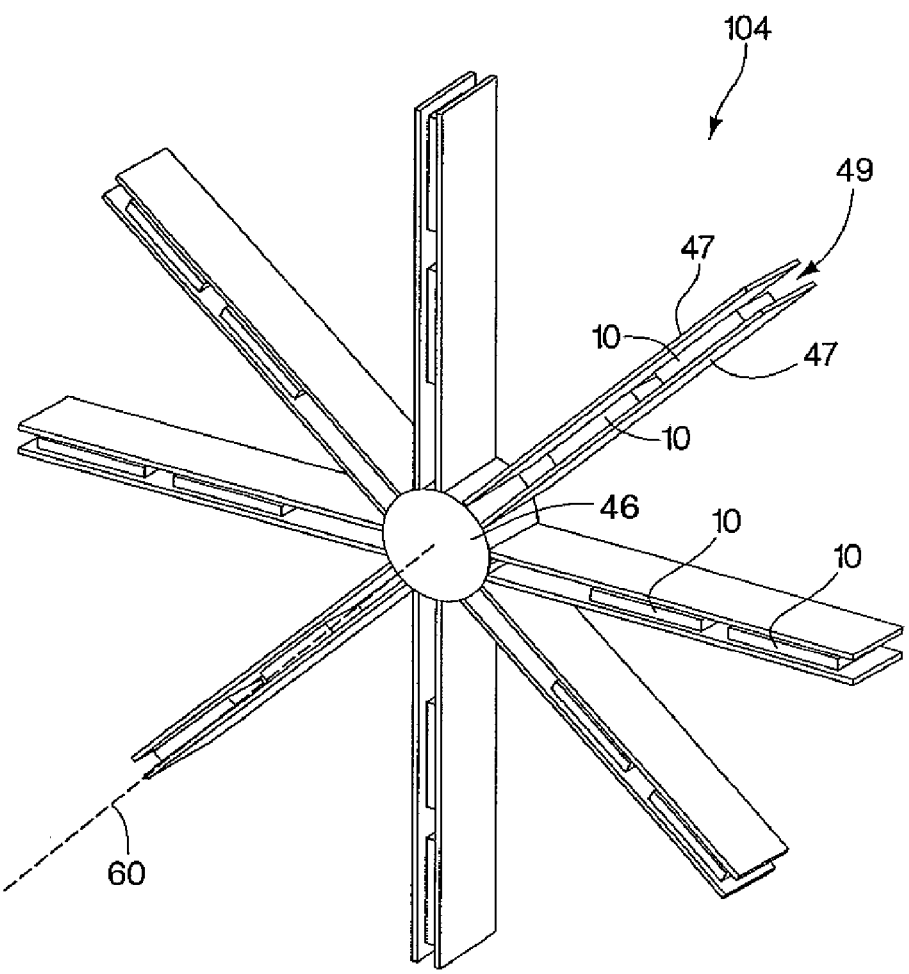
FIG. 4 illustrates an embodiment of the invention configured to be able to secure multiple substrates.

FIG. 4 illustrates a device 104 that can be used in another set of embodiments of the invention. For example, an apparatus using device 104 may be used in the embodiments shown in FIG. 1, 2, or 3. Device 104 may be contained within a housing or incubator, or used as part as a free-standing apparatus. In FIG. 4, pairs of radially outwardly extending members 47 each define a partially enclosed space 49 therebetween, in which one or more chambers 10 can be secured therein. Each of radially outwardly extending members 47 is connected to an axle 46, which is able to rotate about substantially horizontal axis 60. In FIG. 4, device 104 contains 16 radially outwardly extending members 47, defining eight spaces 49 configured to be able to secure chambers; however, in other embodiments, device 104 may include more or fewer radially outwardly extending members 47, and members 47 typically are symmetrically arranged around axle 46. In some embodiments, chambers 10 within partially enclosed space 49 may be secured such that chambers 10 are not able to move, or radially outwardly extending members 47 may be constructed and arranged such that members 47 are able to secure chambers 10 within the device when the device is rotated about substantially horizontal axis 60 such that chambers 10 are not dislodged from the device 104 during operation, but can move within space 49. As device 104 rotates about substantially horizontal axis 60, the orientation of chambers 10 changes (i.e., from an upright to an inverted position); any fluids that may be present within chambers 10 can thus be agitated without the use of active mixing elements.

In the embodiment illustrated in FIG. 5, device 105 is configured to be able to simultaneously (or separately) revolve chambers 10 (or other substrates) about a central substantially horizontal axis 60 and rotate each of chambers 10 about an individual substantially horizontal axis 61. The individual horizontal axes 61 also revolve around substantially horizontal axis 60. In this figure, axle 56 contains a plurality of radially outwardly extending members 58. Each of the radially outwardly members 58 contains a rotatable mechanism 51 which allows an attachment mechanism, such as a clamp 20, to cause a chamber secured to the mechanism to individually rotate. As axle 56 rotates about substantially horizontal axis 60, radially outwardly extending members 58 are also rotated about substantial horizontal axis 60. Rotation of chambers 10 about individual horizontal axes 61 may be synchronized or individually controlled from the rotation of the chambers about the central substantially horizontal axis 60. Synchronization of the two rotational speeds may be used, for example, in embodiments where substantial agitation of the chambers is not desired, or in the embodiments where it is not desired to invert the chambers during use of device 105. In other embodiments, asynchronous control may be desired, for example, when agitation of chambers 10 without the use of active mixing elements is desired, or where chambers 10 are periodically or chaotically inverted during operation of the device.

Figure 6A:
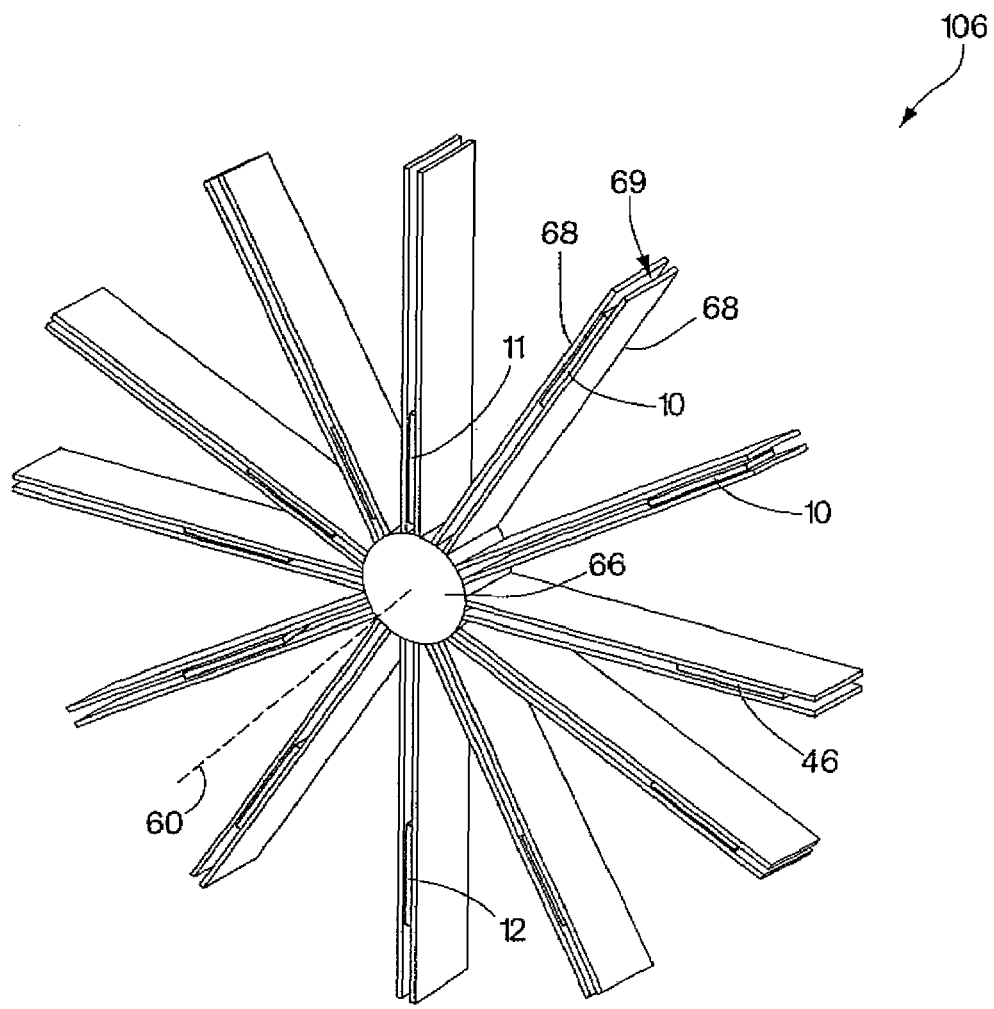
FIGS. 6A-6C illustrate various embodiments of the invention, where a substrate is able to move while secured within an apparatus.
Figure 6B:
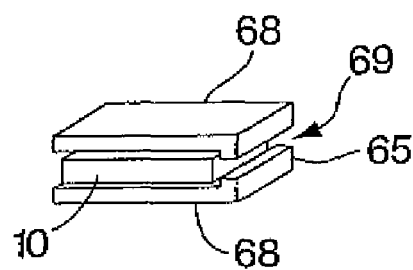
Figure 6C:
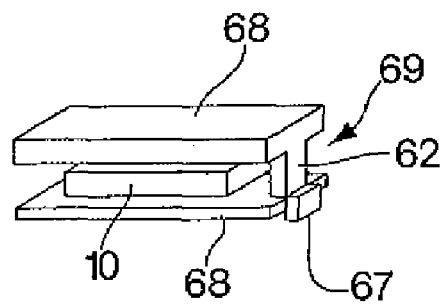

In FIGS. 6A-6C an embodiment of the invention is shown that allows a chamber secured within an apparatus to move. In FIG. 6A, device 106 contains a plurality of radially outwardly extending arms 68 configured to be able to revolve about substantially horizontal axis 60. The radially outwardly extending arms 68 are attached to an axle 66. Pairs of radially outwardly extending arms 68 define spaces therebetween 69 able to contain one or more chambers 10. In this embodiment, space 69 defined therebetween outwardly extending arms 68 secures chamber 10 such that chamber 10 will not be dislodged from device 106 during operation of the device, but does not immobilize chamber 10 with respect to the radial distance away from substantially horizontal axis 60. Thus, in some cases, chamber 10 is free to slide within space 69 defined therebetween outwardly extending arms 68. In some cases, movement of chamber 10 within space 69 may be substantially radially outward from substantial horizontal axis 60; in other embodiments, other types of motion, such as transverse motion, may also be allowed. Movement of chamber 10 within space 69 may occur due to gravity. For example, as device 106 is rotated about substantially horizontal axis 60, the gravitational force on chamber 10 shifts. Thus, chamber 10 may move from a position that is close to substantially horizontal axis 60, shown by position 11, to a position that is further away from substantial horizontal axis 60, shown by position 12. In some cases, other forces acting on chamber 10 may also cause movement of chamber 10 within space 69, for example, mechanical, electrostatic, and/or magnetic forces. As axle 66 rotates about substantial horizontal axis 60, chambers 10 may move within space 69 such that the position and the net force exerted on chambers 10 depends on the angular position of radially outwardly extending arm 68 and space 69 with respect to axle 66.

Each of radially outwardly extending arms 68 may be constructed in such a way as to prevent chamber 10 from leaving device 106 as device 106 moves, thus securing chamber 10 within device 106. For instance, in FIG. 6B, chamber 10 is contained within a space 69 defined therebetween radially outwardly extending arms 68. Chamber 10 is unable to move beyond the ends of radially outwardly extending arms 68 due to a lip 65 on the end of radially outwardly extending arm 68. A similar embodiment is shown in FIG. 6C, where a chamber 10 is contained within space 69 by a restraining member 62 at the end of a radially outwardly extending arm 68. As an example, restraining member 62 may be a post or a series of posts. In some cases, as is shown in FIG. 6C, the end of restraining member 62 may be secured in place by a securing mechanism 67, which may be adjustable and/or removable in certain embodiments. For example, when a chamber is to be removed from space 69, securing mechanism 67 may be disengaged from restraining member 62, allowing restraining member 62 to be moved or rotated away from the end of space 69, thereby allowing chamber 10 to be removed from space 69.

Figure 7A:
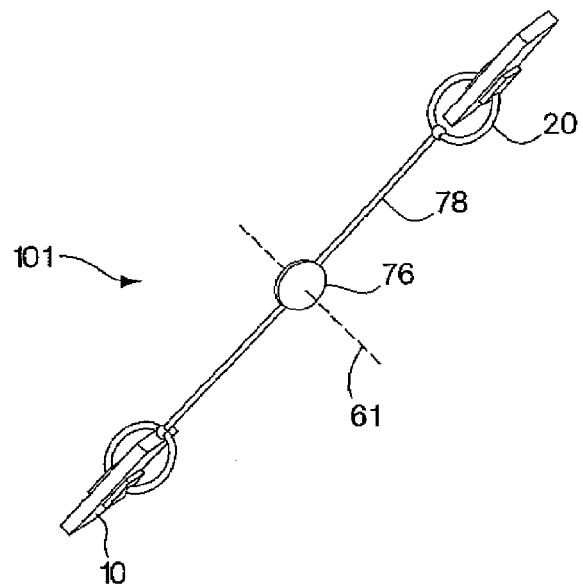
FIGS. 7A and 7B illustrate additional embodiments of the invention configured to be able to revolve a substrate about an axis.
Figure 7B:
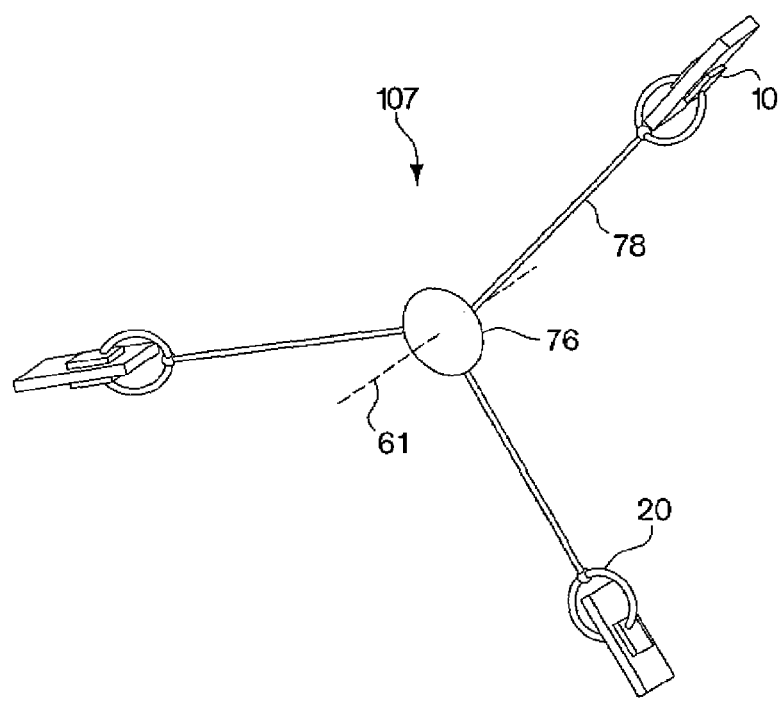

FIGS. 7A and 7B show devices according to other embodiments of the invention, demonstrating that the rotating device may have a wide variety of suitable geometries, while preferably still configured to be able to rotate at least one chamber (or other substrate) about a substantially horizontally axis. For example, in FIG. 7A, apparatus 101 includes an axle 76 and two radially outwardly extending members 78 symmetrically extending away from axial 76. At the end of each of radially outwardly extending members 78 are clamps 20 configured to be able to secure chambers 10. Similarly, in FIG. 7B, axial 76 contains three radially outwardly extending members 78, symmetrically arranged, each containing a clamp 20 configured to be able to secure a chamber 10. In the embodiments shown here, axle 76 is able to rotate about axis 61. Axis 61 may be a substantially horizontal axis, a substantial vertical axis, or in an axis in essentially any direction.

Figure 8:
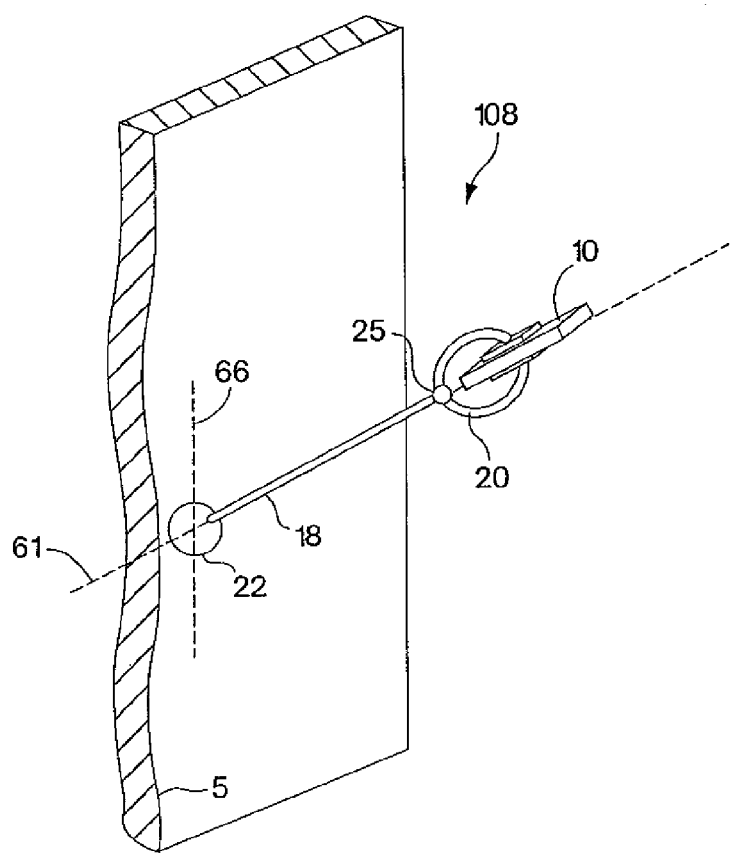
FIG. 8 illustrates another embodiment of the invention configured to be able to revolve a substrate about a fixed point.

In FIG. 8, another embodiment of the invention is shown attached to surface 5. Surface 5 may be a wall, a floor, or other suitable horizontal or vertical surface, for example, the wall of a incubator, the wall of housing, or the wall of a laboratory. Apparatus 108 is attached to wall 5 through attachment mechanism 22. Attachment mechanism 22 can rotate and/or revolve apparatus 108 about one or more axes, for example, substantially horizontal axis 61 and/or substantially vertical axis 66. Suitable rotatable attachment mechanisms will be known to those of ordinary skill in the art. Connected to attachment mechanism 22 may be one or more outwardly extending arms 18, each arm containing one or more clamps 20 (or other suitable attachment mechanisms) able to secure one or more chambers 10 (or other substrates). In some cases, clamp 20 may be able to rotate with respect to radial arm 18 through rotation mechanism 25. In such cases, control of the movement of rotation mechanism 25 may be associated with, or in other cases, independent from, mechanism 22. In certain embodiments, device 108 may not contain mechanism 22.

FIG. 9 illustrates another embodiment of the invention. In FIG. 9, device 109 may be placed on a horizontal or a vertical surface, for example, on the floor, on a counter, or within an incubator or other housing. Device 109 includes a base 30 that rests on a surface (not shown), and, in some cases, may be immobilized or otherwise attached to the surface using any suitable attachment mechanism. Connected to base 30 is rotational mechanism 22, which is configured to rotate a portion of device 109 about a substantially vertical axis 67, as shown in FIG. 9. Rotating mechanism 22 may be any suitable rotating mechanism, and can be selected by those of ordinary skill in the art. Attached to rotational mechanism 22 is a plurality of outwardly extending arms 18, each arm extending radially away from rotating mechanism 22. At the end of the radially outwardly extending arms 18 is rotation mechanism 25 and clamp 20 (or other attachment mechanism). In some cases, rotating mechanism 25 may allow clamp 20 to rotate a chamber 10 (or other substrate) about a substantially horizontal axis 61. This motion about substantially horizontal axis 61 may be associated with, or independent from, the revolution of outwardly extending arms 18 about substantially vertical axis 67. In certain cases, mechanism 25 is absent. In some instances, apparatus 109 may be transportable, for example, such that it can placed within an incubator or other housing.

The apparatuses described may be configured to secure the chamber (or other substrate) in any of a variety of suitable orientations. Depending on the configuration of the chamber, certain such orientations may be particularly advantageous for imparting a desired degree or pattern of mixing or agitation. As explained in more detail below in the context of FIG. 10, this can be especially important for manipulation of articles, chambers, or other substrates comprising one or a plurality of elongate volumetric containers, e.g. for containing a liquid of other fluid, each container having an internal volume defining an elongate predetermined reaction site on or in the article, chamber, or other substrate. "Elongate," as used herein when referring to a predetermined reaction site, refers to a predetermined reaction site having a perimetric shape, e.g. of an outer boundary or container, that is characterized by there being a first straight line segment, contained within the outer boundary/container, connecting two points on the outer boundary/container and passing through the geometric center of the predetermined reaction site that is substantially longer than a second straight line segment, perpendicular to the first line segment, contained within the outer boundary/container, connecting two points on the outer boundary/container—other than the same two points connected by the first line segment—and passing through the geometric center of the predetermined reaction site. For example, if the article is a planar chip comprising a volumetric container defining a predetermined reaction site characterized by a thickness, measured in a direction perpendicular the plane of the chip and a length and width, measured in mutually perpendicular directions both parallel to the plane of the chip, the predetermined reaction site would be "elongate," if the length substantially exceeded the width (e.g. as would be the case for a thin, rectangular or ellipsoidal, tear-shaped, etc., predetermined reaction site). An axis co-linear with the longest such straight line segment, contained within the outer boundary/container, connecting two points on the outer boundary/container and passing through the geometric center of the predetermined reaction site for an elongate predetermined reaction site is referred to herein as the "longitudinal axis" of the predetermined reaction site.

For example, in FIG. 10A, chamber(s) 10, comprising a plurality of elongate volumetric containers 7 defining elongate predetermined reaction sites 8, each characterized by a longitudinal axis 9, is secured to an apparatus 3 configured to revolve the chamber about a substantially horizontal axis 60. Chamber(s) 10 is secured to apparatus 3 such that the longitudinal axes 9 of predetermined reaction sites 8 are arranged with respect substantially horizontal axis 60 so that longitudinal axes 9 are parallel to horizontal axis 60. In a preferred arrangement, shown in FIG. 10B, chambers 10 are secured to apparatus 3 such that the longitudinal axes 9 of predetermined reaction sites 8 are arranged with respect substantially horizontal axis 60 so that longitudinal axes 9 are perpendicular to and non-intersecting with substantially horizontal axis 60. In the configuration illustrated in FIG. 10C, chamber 10 is secured to apparatus 3 such that the longitudinal axes 9 of predetermined reaction sites 8 are arranged with respect substantially horizontal axis 60 so that longitudinal axes 9 are perpendicular to and interest with substantially horizontal axis 60.

As described in U.S. patent application Ser. No. 11/147, 413, and as shown in FIGS. 11A- 11C, chips 11 including reaction site container 28 may be mounted to a rotating apparatus 53, such as described above, When rotating apparatus 53 rotates, the orientation of chip 11 relative to gravity changes and immiscible substances of different densities move relative to one another within reaction site container 28. FIG. 11A shows a radial mounting orientation for a chipjpntaining six reaction site containers 28. As chip 11 revolves around axis 51 via the rotation of rotating apparatus 53, an immiscible substance 17 moves no and down relative to gravity which results in lateral movement within reaction site container 28, as shown in FIG. 12A. Immiscible substance 17 may reach the side walls of reaction site container 28 depending on the rotation rate and the relative densities of immiscible substance 17 and the liquid sample. At high rotation rates, immiscible substance 17 does not have time to move entirely to one side wall before reaction site container 28 is reversed relative to buoyancy or gravitational forces, and immiscible substance 17 moves in the opposite direction. At slower rotation rates or higher density differences, immiscible substance 17 moves faster and may reach one side wall before the reaction site container orientation is reversed.

FIG. 11B shows a vertical mounting orientation for three chips 11 on rotating apparatus 53. In this embodiment, inumiscible substance 17 tends to follow a circuitous path within container 28 when chip 11 is revolved around axis 51, as shown in FIG. 12B. Such a path may help re-suspend cells or other species that have attached or sealed along the inside perimeter of container 28. Similar to the embodiment of FIG. 11A, the extent of travel of immiscible substance 17 denends on the rotation rate and the relative densities of immiscible substance 17 and the liquid sample.

FIG. 11C shows a horizontal orientation for mounting chip 11 on rotating apparatus 53. In this orientation, immiscible substance 17 moves in an end-to-end direction during rotation. Similar to the embodiments of FIGS. 11A and 11B, the extent of travel of immiscible substance 17 depends on the rotation rate and the relative densities of immiscible substance 17 and the liquid sample.

The apparatuses described may be configured to secure the chip, article, or other substrate in any of a variety of suitable orientations. Depending on the configuration of the chip, article, or other substrate, certain such orientations may be particularly advantageous for imparting a desired degree or pattern of mixing or agitation. As explained in more detail below in the context of FIGS. 11A-11C, this can be important for manipulation of articles comprisina one or a plurality of elongate containers.

For example, in FIG. 11A, a chip 11, comprising a plurality of elongate containers 28, such as biological containers (for example, defining a predetermined reaction site), each characterized by a longitudinal axis, is secured to rotating apparatus 53 configured to revolve the article about a substantially horizontal axis 51. Chip 11 is secured to apparatus 53 such that the longitudinal axes of containers 28 arc arranged with respect substantially horizontal axis 53 so that the longitudinal axes are parallel to horizontal axis 51. In a preferred arrangement, shown in FIG. 12B, chips 11 are secured to apparatus 53 such that the longitudinal axes of containers 28 are arranged with respect to substantially horizontal axis 51 so that the longitudinal axes are perpendicular to and non-intersecting with substantially horizontal axis 51. In the configuration illustrated in FIG. 12C, chip 11 is secured to apparatus 53 such that the longitudinal axes 19 of containers 29 are arranged with respect substantially horizontal axis 53 so that the longitudinal axes are perpendicular to and intersect with substantially horizontal axis 51.

In certain embodiments of the invention, housing 40 may be an incubator in which cells or other biological samples can be readily cultured or grown. For example, housing 40 may be a commercially available or custom-built incubator, and a device for securing and/or rotating or revolving articles, chambers, or substrates may be placed within the incubator, for example, on a shelf of the incubator, or on an inside floor of the incubator. In another set of embodiments, a device for securing and/or rotating or revolving articles, chambers or substrates may be secured within a housing, for example to stabilize and/or position the device within the incubator. As an example, the device may be connected to a wall of a housing, as shown in FIG. 8. In one set of embodiments, the housing may be a custom-designed housing able to hold the device. For example, a custom-designed housing may house a device able to contain or secure a relatively large number of articles, chambers, or substrates. In some cases, the housing may be designed to have a relatively small "footprint" area, for instance, to save space within a laboratory.

Conditions for operating an incubator can be readily determined by those of ordinary skill in the art. For example, the incubator may be designed to be able to maintain a constant temperature therein, for example, a temperature of about 32° C. or about 37° C. The incubator may also be designed to maintain a certain relative humidity within the incubator, for example, a relative humidity of greater than about 90%, greater than about 95%, or about 100% (i.e., essentially saturated humidity). In certain cases, the incubator may be designed to control the concentration of one or more gases therein, for example, a gas necessary for cell metabolism, such as oxygen, carbon dioxide, or nitrogen. Sensors, processors, valves, or the like may be used within the incubator to control some or all of the environmental conditions therein.

In one aspect of the invention, access port 50 may be only large enough to readily admit one or a small number of articles, chambers or other substrates at a time. In one set of embodiments, the access port includes a minimum cross-sectional dimension less than about 4 times, less than about 3 times, less than about 2 times, less than about 1.5 times, or less than about 1.2 times the minimum dimension of the article, chamber or other substrate to be introduced into the access port. A smaller access port may be advantageous, for example, in cases where control of the internal environment of the incubator is desired. A smaller access port may minimize the exchange of gases and/or changes in environmental conditions between the incubator and the external environment around the incubator, for instance, while articles, chambers or other substrates are being added to or removed from the incubator. The access port may be designed in some embodiments such that an operator such as a user or an external mechanism (e.g., a robotic instrument) is able to add or remove one or a small number of articles, chambers or substrates from the apparatus at a time. Examples of such external mechanisms are described in U.S. patent application Ser. No. 10/457,017, filed Jun. 5, 2003, entitled "System and Method for Process Automation," by Rodgers, et al., or a U.S. patent application filed on even date herewith, entitled "System and Method for Process Automation," by Rodgers, et al., each incorporated herein by reference.

The access port may be controllable in some cases, for example, between an open state and a closed state. For example, the access port may be normally closed, but be openable as needed by an operator (e.g., a user or a handling apparatus), for example, at certain preset times (such as with a door). In some cases, the access port to the incubator may include an airlock, e.g., an apparatus having two or more doors that have to be opened and closed in series in order for internal access to occur. In certain instances, the access port may be controlled through the use of self-sealing materials (i.e., a material that will not allow a liquid or a gas to readily pass therethrough without the application of an external driving force, but will admit the insertion of a mechanical apparatus able to penetrate the material). Examples of self-sealing systems include plastic flaps that cover the access port when the access port is not in use, or a material that blocks the access port and can be mechanically penetrated as desired.

In certain embodiments an apparatus of the invention may be sterilizable in some fashion. In certain embodiments, the apparatus may include a sterilizable material, i.e., a material that can repeatedly withstand sterilizing conditions without significant degradation. In one embodiment, the apparatus is an incubator, optionally including a device for manipulating chambers and other substrates. The apparatus may be sterilizable in some fashion, for example, to kill or otherwise deactivate biological species therein (e.g., cells, bacteria, viruses, etc.), before the apparatus is used or re-used. For instance, the apparatus may be sterilized with chemicals, radiated (for example, with ultraviolet light and/or ionizing radiation), heat-treated, or the like. Appropriate sterilization techniques and protocols are known to those of ordinary skill in the art. For example, in one embodiment, the apparatus is autoclavable, i.e., the apparatus includes materials able to withstand commonly-used autoclaving conditions (e.g., exposure to temperatures greater than about 100° C. or about 120° C., often at elevated pressures, such as pressures of at least one atmosphere), such that the apparatus, after sterilization, does not substantially deform or otherwise become unusable. Another example sterilization technique is exposure to ozone.

As one example of a sterilizable apparatus, the apparatus may be formed from or include a metal or metal alloy able to withstand temperatures of at least about 100° C. or about 120° C., for example, copper or stainless steel. Copper may be particularly useful in some embodiments, as copper may discourage the growth of some fungi. As another example, the metal may include titanium or aluminum. In some cases, the apparatus and/or incubator may be formed from other materials able to withstand temperatures of at least about 100° C. and/or other autoclaving conditions, for example, the apparatus may include ceramics, composites such as metal composites, or certain polymers that may be heat-resistant. Other suitable materials for use in the apparatus and/or device can be selected by those of ordinary skill in the art.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus, comprising:
   a selection region;
   a device able to simultaneously agitate and revolve a plurality of substantially planar biological substrates about a substantially horizontal axis that does not pass through the substantially planar biological substrates such that the substantially horizontal axis is substantially orthogonal to the plane of the substantially planar biological substrates when the substantially planar biological substrates are mounted within the device, wherein the device is able to selectively position at least one of the biological substrates in the selection region; and
   an access port sized such that a planar biological substrate may be admitted into the selection region, and wherein the access port allows transfer of the planar biological substrate into and out of the selection region in a direction substantially perpendicular to the substantially horizontal axis.

2. An apparatus as in claim 1, wherein a cell culture chamber comprises the biological substrate.

3. An apparatus as in claim 1, further comprising a housing surrounding the device.

4. An apparatus as in claim 3, wherein the selection region is defined by an opening in the housing surrounding the device.

* * * * *